US005348004A

United States Patent [19]

Hollub

[11] Patent Number: 5,348,004
[45] Date of Patent: Sep. 20, 1994

[54] ELECTRONIC PROCESSOR FOR PULSE OXIMETER

[75] Inventor: Seth D. Hollub, Overland Park, Kans.

[73] Assignee: Nellcor Incorporated, Pleasanton, Calif.

[21] Appl. No.: 40,839

[22] Filed: Mar. 31, 1993

[51] Int. Cl.$^5$ .............................................. A61B 5/00
[52] U.S. Cl. ................................ 128/633; 128/664; 128/666; 356/41
[58] Field of Search ........................... 128/633–634, 128/664–667; 356/39–41

[56] References Cited

U.S. PATENT DOCUMENTS

| | | |
|---|---|---|
| 2,706,927 | 4/1955 | Wood . |
| 4,086,915 | 5/1978 | Kofsky et al. . |
| 4,394,572 | 7/1983 | Wilber .............................. 128/633 |
| 4,407,290 | 10/1983 | Wilber .............................. 128/633 |
| 4,603,700 | 8/1986 | Nichols et al. ................ 128/665 X |
| 4,653,498 | 4/1989 | New, Jr. et al. ................ 128/633 |
| 4,653,498 | 3/1987 | New, Jr. et al. ................ 128/633 |
| 4,759,369 | 7/1988 | Taylor ........................... 128/664 X |
| 4,781,195 | 1/1988 | Martin ........................... 128/633 |
| 4,846,183 | 7/1989 | Martin ........................... 128/633 |
| 4,927,264 | 5/1990 | Shiga et al. ................... 128/633 X |

Primary Examiner—Angela D. Sykes
Attorney, Agent, or Firm—Townsend and Townsend Khourie and Crew

[57] ABSTRACT

An electronic processor for calculating in vivo blood oxygenation concentration levels using pulsed light that eliminates both requirements for comparing photosensor signal amplitudes with analog/digital circuit dynamic ranges and also adjusting electronic processor parameters. The invention uses monolithic a/d converters with expanded capacity and a microcontroller/processor with a pulse control module to synchronize switching in an oversampling demodulator with pulsing of light sources to overcome prior circuitry limitations that consumed substantial central processor capacity.

23 Claims, 3 Drawing Sheets

ELECTRONIC PROCESSOR FOR PULSE OXIMETER

TECHNICAL FIELD

This invention generally relates to making in vivo measurements of blood constituent concentrations, such as hemoglobin oxygen saturation, using optical multi-wavelength pulse spectrometers, for example pulse oximeters, that direct light of two or more wavelengths into living tissue and measure attenuation of scattered light through either forward-scattering (transmission mode) or back-scattering (reflection mode) to determine blood constituent concentrations including hemoglobin oxygen saturation.

BACKGROUND ART

Insufficient blood oxygenation, known as hypoxemia, can cause irreversible injury or even death. For example, surgical patients are vulnerable to hypoxemia during anesthesia. Similarly, hypoxemia may occur during recovery from anesthesia, during critical care treatment (also known as intensive care), and at other times when patient airway functions or cardiopulmonary functions may be compromised during periods of medical care on hospital general medical/surgical wards or during home care. A patient may be particularly vulnerable when dependent on supplemental oxygen or an artificial airway. Early warnings of hypoxemia, in these and other situations if adequately provided, can permit clinicians sufficient opportunity to intervene and prevent occurrence of irreversible injury. Examples of monitoring equipment that have been used to provide warnings of the onset of hypoxemia include non-invasive multi-wavelength spectrometers, such as pulse oximeters. Pulse oximeters are used by anesthesiologists, surgeons, critical care physicians, emergency medical physicians and other clinicians, including home care providers. To effectively provide warning though the equipment must be capable of continuous, accurate and real time measurement of patient hemoglobin oxygen saturation.

Since the mid-1930s it has been known that attenuation measurements of light passed through blood, either in vivo or in vitro, can be used to determine hemoglobin oxygen saturation, i.e., blood oxygenation concentrations. Technologies for such measurements rely on the fact that hemoglobin in blood can be loosely combined with oxygen in the form of oxyhemoglobin for transport to various body tissues where oxygen can be released. This chemistry supports in vivo optical measurements of blood oxygenation concentrations because light extinction factors, i.e., the magnitudes of attenuation, for oxyhemoglobin are different from that for hemoglobin. For example, hemoglobin transmits much less visible red light (620–770 nanometers (nm)) than does oxyhemoglobin. Therefore, blood with high oxygen concentrations will transmit more visible red light than will blood with low oxygen concentrations. On the basis of these facts oximeter instruments using pulsed light sources in combination with photosensors to measure light intensities transmitted through patient tissue have been developed for determining in vivo blood oxygenation concentrations. In general such oximeter instruments include a photoelectric probe and an electronic processor. Typically, the photoelectric probes, which include light sources and photosensors, are positioned on a patient so light can be directed to pass through tissue, i.e., forward-scattered, before being received by photosensors. Convenient locations for mounting these photoelectric probes on patients include fingers and ears. Alternative photoelectric probes rely on back-scattering to effect light attenuation for determining blood constituent concentrations. Electronic processors for oximeter instruments are used in conjunction with photoelectric probes of either type for controlling power to light sources, measuring photosensor detected light signal waveform amplitudes, determining attenuation of light passed into patient tissue, and providing read outs of blood oxygenation concentration levels determined from identified attenuation magnitudes. A pulse oximeter of this general type is disclosed in U.S. Pat. No. 4,621,643 to New, Jr., et al.

Today, pulse oximeters are virtually standard equipment in hospital operating rooms and other facilities, such as intensive care units, where patients require real time accurate in vivo monitoring of blood oxygenation concentration levels. In fact, there is now a recognized and accepted critical requirement for real time accurate in vivo monitoring of blood oxygenation concentration levels. Specifically, the need and the commensurate capability provided by pulse oximeters resulted in a 1986 issuance of standards recommending use of pulse oximeters by the American Society of Anesthesiologists. Accordingly use of pulse oximeter equipment is rapidly expanding into hospital general medical/surgical wards and is also developing an acceptance as a requirement for home care.

To be effective oximeter electronic processors must be as fully automated as possible for unattended operation over extended periods of time so there is provision of as near real time continuous accurate blood oxygenation concentration measurements as possible. These requirements are integral with situations where such instruments are needed. For example, during surgery anesthesiologists and other physicians need current accurate in vivo information on patient blood oxygenation concentration levels over extended periods of time and this information must be made available with minimum to preferably no requirements for manual adjustment of oximeter equipment. With such automated capabilities for real time, continuous, accurate measurements, physicians and other medical personnel can have essential blood chemistry information while attending to other tasks required for patient care.

Providing automated operation of oximeter equipment requires use of calculating and control circuitry integrally provided by central processor units (CPU). The CPU in such equipment is not only used for commanding display of determined blood oxygenation concentration levels and calculating these levels using measured light intensities, but also for adjusting: light intensity levels prior to transmission into patient tissue; circuitry gains for measuring light intensities; and, can even be required for adjusting rates for sample-and-hold (s/h) circuits and analog-to-digital (a/d) converters. All tasks associated with automation consume time and CPU calculating capacity. In fact, electronic circuitry in current oximeter electronic processors requiring automated monitoring and adjustment necessitate extensive use of hardware and software accordingly reducing the amount of processor time and capacity available for processing measured light signal waveform levels and providing improved oximeter accuracy. Consequently, use of CPU capacity for real time performance and expanded calculations for achieving ultimate accuracy must be traded off against functions required for automated operation.

Critical to both consumption of CPU capacity and instrument accuracy are s/h and a/d circuits used in oximeter electronic processors. In order to maximize accuracy, these circuits can require both adjustment of their sample rates to optimize digitizing of measured light signal waveforms for CPU processing, and also adjustment of associated circuitry gains, to include drive circuits for controlling generated light source intensities. Adjustment of light source intensity can be used to assist s/h and a/d circuits in covering dynamic ranges consumed by measured light signal waveform amplitudes. This later aspect of being able to cover measured light signal waveform dynamic ranges has a direct effect on accuracy in determining blood oxygenation concentration levels. In particular, s/h circuits available at reasonable cost do not have sufficient capacity to adequately cover dynamic ranges needed for measuring light intensity signal waveform amplitudes without implementing automated adjustment of currently used associated circuitry gains. Even with such automated adjustment, however, current oximeter electronic processors must trade off accuracy against required dynamic range coverage because of s/h limitations.

DISCLOSURE OF THE INVENTION

Today, standard pulse oximeters use photoelectric probes with multiple light sources and a photosensor. Light emitting diodes (LEDs) are often used on these photoelectric probes for light sources to produce, for example, visible red light and infrared radiation. In use, such LEDs are serially pulsed to produce interleaved signal streams for detection by the photosensor. The interleaved signal streams can consist of visible red light, noise, infrared radiation, noise etc. All other types of ordering are possible. The invention can be beneficially used with such photoelectric probes, or can be used with any other oximeter photoelectric probe incorporating electrically powered pulsed energy sources and sensors.

As discussed above oximeter electronic processors were previously dependent on significant percentages of CPU capacity for implementing necessary automated circuit adjustment. Invariably, however, such adjustments of light output intensities and amplifier gains also result in causing settling times that must be expended before consistent reliable data can be provided. Therefore minimizing circuit parameter adjustments so settling times are minimized is another related important goal. Patient motion, though, is an example of an unavoidable real environmental occurrence that has, until this invention, required repeated compensatory circuit adjustments. Accordingly automated adjustments need to be optimized when feasible by, for example, taking dynamic signal trends into consideration so as to minimize settling times. Such automated adjustment optimization is yet another processing need that rapidly consumes CPU capacity.

In contrast to prior circuitry that consumed substantial CPU capacity with automated circuit adjustment, an embodiment of this invention provides efficient functional adjustment by use of two autonomous sections of a microcontroller/processor unit (MPU). These two autonomous sections are a pulse control module and a queued serial input module. Both of these modules interface with a CPU through a random access memory (RAM) to form the MPU. As used with other circuits of the invention, discussed below, these two autonomous MPU sections provide all necessary control for automated operation and, therefore, allow the CPU to be dedicated to other tasks, including real-time processing of the entire dynamic range of measured light signal waveform amplitudes with improved accuracy.

Along with the MPU, oximeter electronic processors of the invention also use synchronous detection with an oversampling demodulator for each signal stream, i.e., visible red light, infrared etc. Included as part of the oversampling demodulator is an analog switch. Detected light signal waveforms are fed from the photoelectric probe photosensor into temporally controlled analog switches for synchronous detection. One of the outputs from each analog switch is connected to ground. Each analog switch is followed by a low-pass filter with a wide range a/d converter. Outputs from these a/d converters interface with the MPU through the queued serial input module. It is this interface that is used to provide data to the CPU. The only other use of this interface between the queued serial input module and the CPU is for initialization and recalibration of a/d circuits.

The remaining interfaces with the MPU of the invention are from the pulse control module to the LED drive circuits that have fixed gains and the analog switches. The interface here is exclusively used to send timing signals to the LED drive circuits. Establishment of these timing signals can be a one time operation initiated from the CPU and sustained by the pulse control module. During operation, but after initialization, adjustment of timing signals by the CPU to overcome ambient environmental noise, such as electrical noise, optical interference, or patient movement, may, however, be necessary.

Oximeters using this invention with a MPU, synchronous detection and oversampling demodulators remove the requirements for a CPU having to perform light signal waveform saturation calculations and commensurately controlling adjustment of signal measuring circuit gains. Effecting these functions by non-CPU circuitry in MPUs and synchronously controlled oversampling demodulators not only eliminates unreliable initial readings caused by erroneous CPU prescaler calculations providing inaccurate saturation data estimates, but also minimizes if not eliminates the need for external adjustments, for example, when patients and their monitoring oximeter equipment are moved.

BRIEF DESCRIPTION OF THE DRAWINGS

The various objectives, advantages and novel features of the invention will become more readily apprehended from the following detailed description when taken in conjunction with the appended drawings, in which.

BEST MODE FOR CARRYING OUT THE INVENTION

Figure 1:
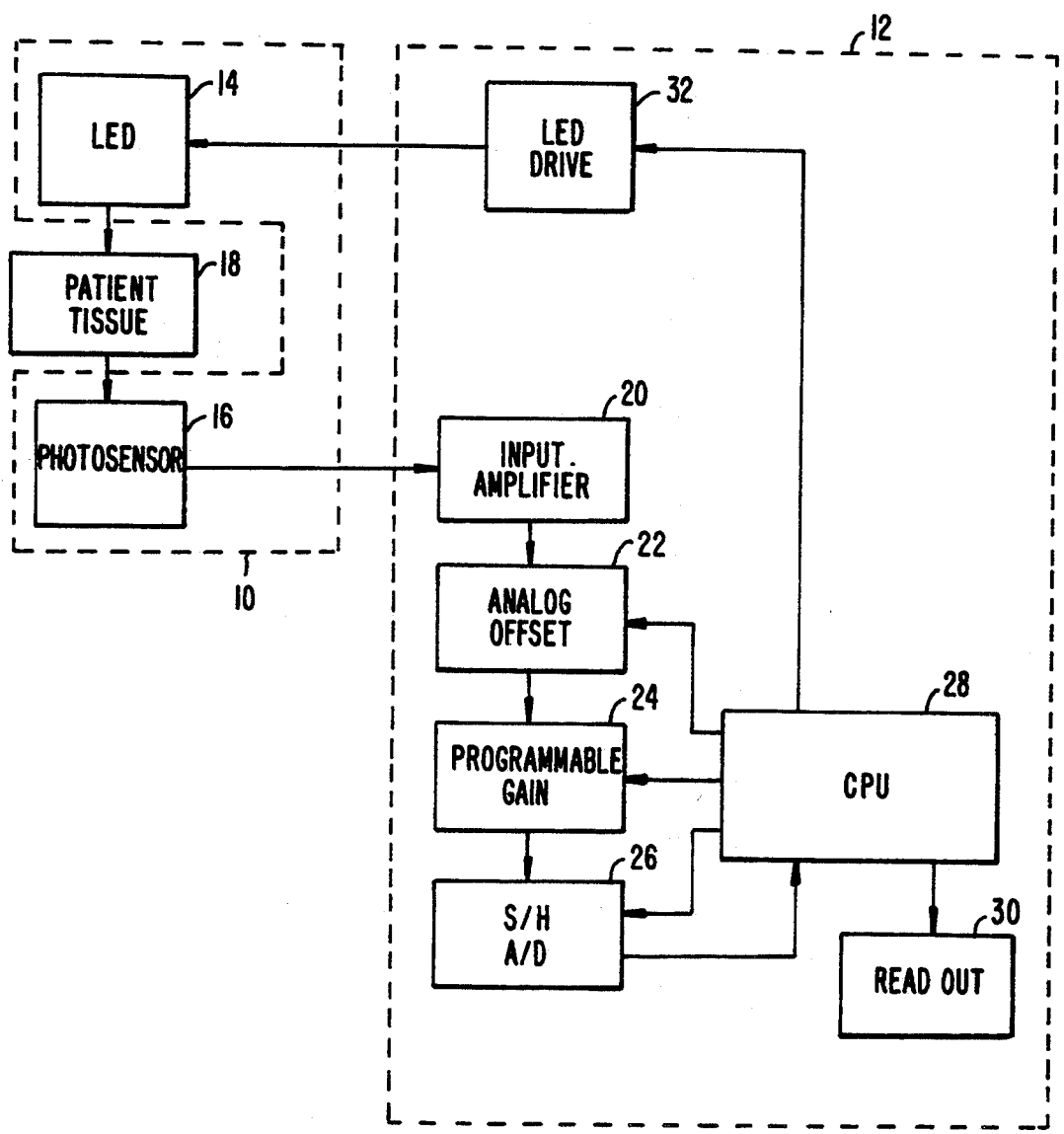
FIG. 1 is a block schematic diagram illustrative of prior pulse oximeter equipment including electronic processor designs.

Referring now to the drawings—where corresponding components are designated by the same reference numerals throughout the various figures—a block schematic diagram illustrative of prior pulse oximeter equipment is shown in FIG. 1. Major components for such oximeter equipment are a photoelectric probe 10 and electronic processor 12. The photoelectric probe 10 includes one or more LEDs 14 and a photosensor 16.

In use, light from LEDs 14 passes into patient tissue 18 and after either being transmitted or backscattered is received by photosensor 16. The received light signal waveform is fed to input amplifier 20, which is usually a fixed gain amplifier used to provide sufficient signal amplitude for processing by subsequent circuitry and also buffer received signals. From the input amplifier 20 the signal is provided to an analog offset 22 circuit used to control signal polarity and optionally adjust light signal waveform amplitudes as required. At this point light signal waveform amplitudes are additionally adjusted by programmable gain 24 circuitry. Such light signal waveform amplitude adjustment is required for processing by s/h and a/d 26 circuitry, because excessive amplitude levels will be clipped by the s/h and a/d 26 circuits when their dynamic ranges are insufficient. Such clipping eliminates and therefore provides inaccurate light signal waveform amplitude data to the CPU 28, and results in uncorrectable errors in determining blood oxygenation concentration levels for display on read out 30.

To address this situation with prior oximeter electronic processors 12, the CPU 28 must be used to compare inputted light signal waveform amplitudes with dynamic ranges of the s/h and a/d 26 circuits. When light signal waveform amplitudes approach limits of s/h and a/d 26 dynamic ranges the CPU 28 must be used to adjust multiple electronic processor 12 parameters to constrain light signal waveform amplitudes within the s/h and a/d 26 dynamic ranges. Namely, the CPU 28 is required to adjust: (i) power provided from LED drive 32 circuit to the LEDs 14; (ii) gains for the analog offset 22 and programmable gain 24 circuits; and, (iii) possibly rates of signal processing for the s/h and a/d 26 circuits.

Critical to both accuracy and consumption of CPU 28 capacity is signal amplitude dynamic ranges that can be covered by a/d circuits. Until recently there was a serious limit on signal amplitude dynamic ranges that could be accurately covered with reasonably priced circuits. Such circuits typically have a 12 bit capacity, as does the ADC0805 a/d circuits sold by National Semiconductor. Having a 12 bit capacity for a/d circuits is insufficient for light signal waveform amplitudes that must be accurately processed by oximeters. To address this situation prior oximeter electronic processors 12 provided an additional 12 bits of processor capacity by having the CPU 28 dynamically calculate and set power level and circuit gains as described above. However, as also explained above such use of CPU 28 capacity unavoidably degrades overall oximeter performance.

Recently a new type of affordable monolithic a/d converter with expanded capacity has become available. These a/d converters are known as wide range a/d converters, e. g. AD 7710 circuits as supplied by Analog Devices, Inc. Using 60 sample per second 19–24 bit conversion capacities, these new monolithic a/d converters can accurately sample the entire dynamic range of an oximeter photosensor output as processed by associated circuitry.

In contrast, however, reasonably priced currently available s/h devices only have comparable capacities up to about 16 bits which with prior oximeter circuitry still necessitates intensive use of CPU capacity for circuit parameter adjustment.

Figure 2:
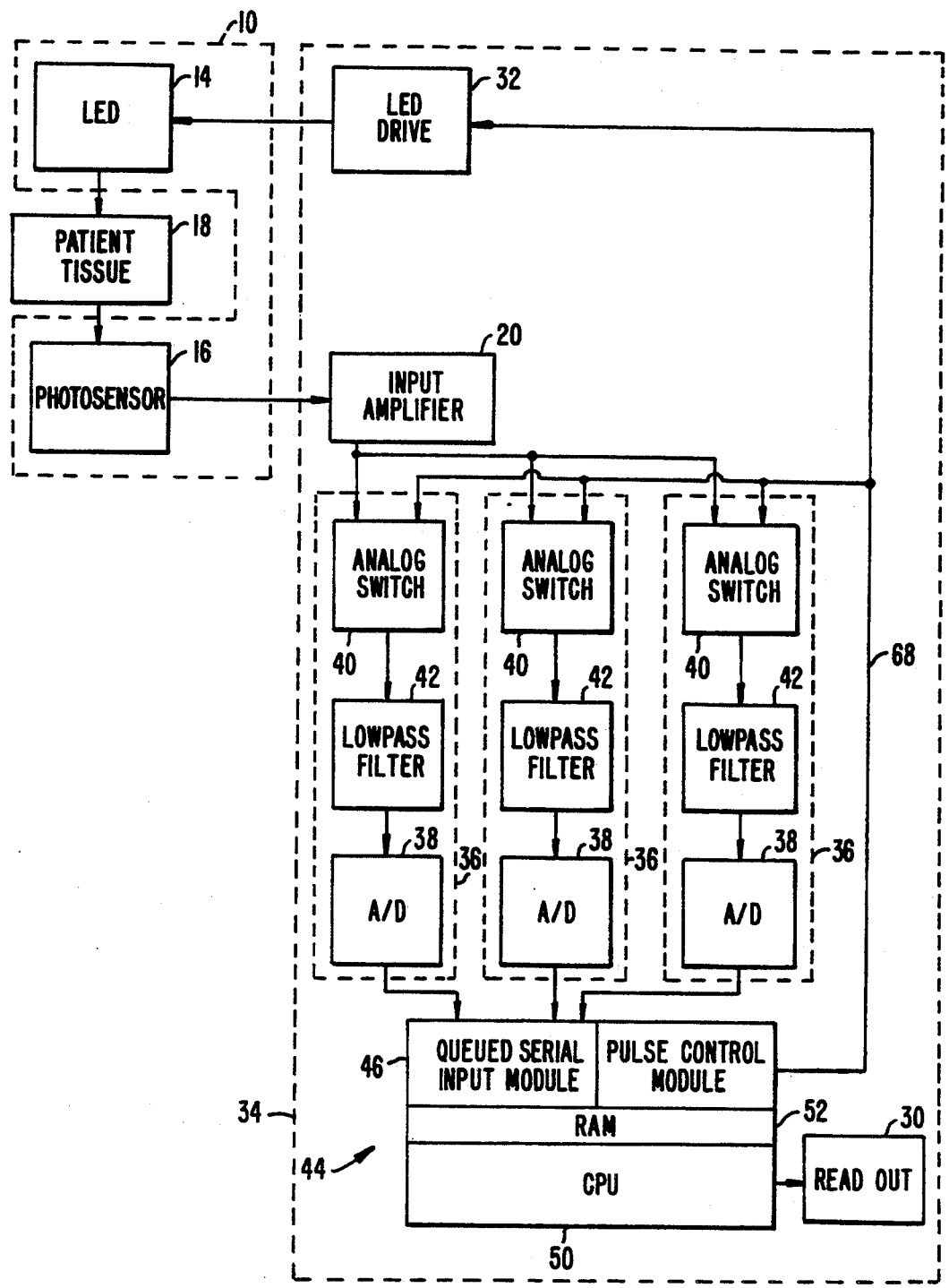
FIG. 2 is a block schematic diagram illustrative of pulse oximeter equipment including oversampling demodulator and MPU circuitry of the invention; and, FIG. 3 is a schematic diagram of an oversampling demodulator according to the invention.

The invention not only both capitalizes on increased a/d conversion capacities and eliminates excessive use of CPU capacity for electronic processor parameter adjustment but also eliminates the need for s/h circuits. FIG. 2 shows an embodiment of pulse oximetry circuitry according to the invention. Common to both prior oximeter equipment and the invention is the photoelectric probe 10 with included LEDs 14 and photosensor 16. The photoelectric probe 10 serves the same functions and provides the same information here, for the invention, as for prior oximeter equipment. Also common to both prior oximeter equipment and the invention are the input amplifier 20 with its fixed gain, and readout 30.

Figure 3:
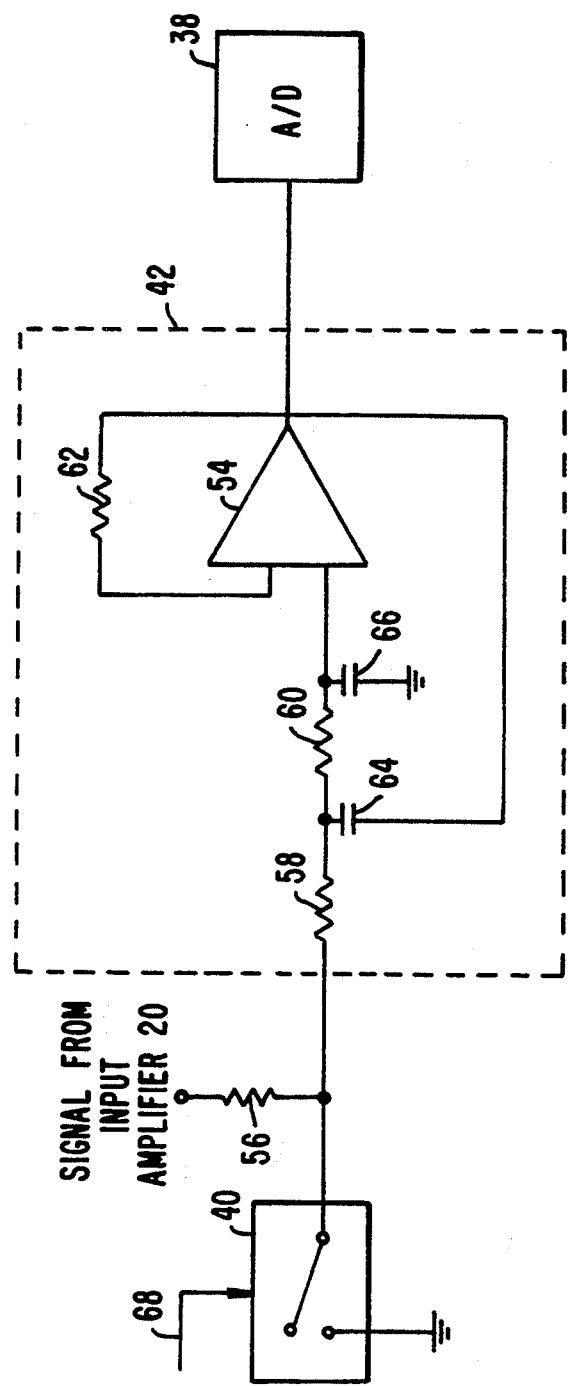

The electronic processor 34 of the invention is provided light signal waveforms from the photosensor 16 which are processed by the input amplifier 20 with a fixed gain. This gain on a voltage basis can be from 35db to 45db. Again this input amplifier 20 provides sufficient signal amplitude for processing by subsequent circuitry and also buffers processed signals. After processing by the input amplifier 20 the light signal waveform is provided to oversampling demodulators 36. Included in each oversampling demodulator 36 a wide range a/d 38 converter which is capable of 19–24 bit conversion. These a/d 38 converters can be AD7710 circuits as supplied by Analog Devices, Inc. The wide range a/d 38 converters are used in the oversampling demodulators 36 without s/h circuits or the need for adjustment of circuit gains. Consequently, dynamic ranges for light signal waveform amplitudes must be processed by the oversampling demodulators 36 so as not to exceed wide band a/d 38 conversion capacities. To achieve this capability, light signal waveforms, which can have a 200 KHz bandwidth when pulsed visible red light and infrared radiation LEDs 14 are used, are first processed by an analog switch 40. Switching rates for analog switch 40, which can be an ADG221 as supplied by Analog Devices, Inc., should be about ten times greater than LED 14 cycle rates. For example, with LED 14 cycle rates of 1.6 KHz the switching rates should be at least 16 KHz. This switching is between ground and a channel that includes a low-pass filter 42. A filter cutoff frequency of about 15 Hz for low-pass filter 42 has been found appropriate for rejecting noise while still passing signals representative of blood oxygenation concentration level fluctuations. A circuit diagram for a useful oversampling demodulators 36 according to the invention is set out in FIG. 3. The analog switch 40 can be an ADG221 as supplied by Analog Devices, Inc., the operational amplifier 54 for the filter can be a TL084 as supplied by Analog Devices, Inc., and the a/d converter 38 can be a AD7710 as supplied by Analog Devices, Inc. Typical values for resistors and capacities in the oversampling demodulator 36 shown in FIG. 3 are set out in Table I.

TABLE I

| Resistor | Value | Capacitor | Value |
| --- | --- | --- | --- |
| 56 | 15kΩ | 64 | 0.01 μF |

TABLE I-continued

| Resistor | Value | Capacitor | Value |
| --- | --- | --- | --- |
| 58 | 11.5kΩ | 66 | 0.01 μF |
| 60 | 10kΩ | | |
| 62 | 10kΩ | | |

In operation the output from photosensor 16 is a current signal. Input amplifier 20 however can be operated to convert this to a voltage signal. Therefore, the configuration for analog switch 40 shown in FIG. 3 provides switching of the input signal between ground and the low-pass filter 42 which is operated in a high impedance voltage mode. This processing in combination with a 50-60 Hz sample rate for wide range a/d 38 converters permits complete coverage of light signal waveform amplitude dynamic ranges for blood oxygenation concentration measurements. As so operated the a/d 38 converters include internal digital low-pass filtering. For example, 15 Hz analog low-pass filters 42 in front of the a/d 38 converters act as anti-aliasing filters for the a/d 38 converters.

Advantages of this oversampling demodulator 36 circuit include: (i) significant noise rejection because of high frequency switching rates that are far from power line harmonics; (ii) elimination of s/h circuits so unclipped light signal waveform amplitudes are provided to low-pass filters 42; and, (iii) use of wide range a/d 38 converters.

A MPU, generally designated by the numeral 44, is used in the electronic processor 34 of the invention. This MPU 44 includes a queued serial input module 46 and a pulse control module 48. These two modules interface with a CPU 50 through a RAM 52. A commercially available and useful MPU for the invention is sold by Motorola as a MC68HC16. This device includes the necessary queued serial input module 46, pulse control module 48, RAM 52 and CPU 50 for the invention.

The outputs from wide range a/d 38 are provided to queued serial input module 46 for input to the CPU 50 through RAM 52 as shown in FIG. 2. While a timing signal is provided from pulse control module 48 to a fixed power output LED drive 32 circuit. This timing signal is initially set by the CPU 50 and is sustained by the pulse control module 48. To implement synchronous detection the timing signal is also used for controlling operation of analog switches 40. Specifically, an oversampling demodulator 36 can be used for each signal type to be processed. For example, if visible red, infrared and noise signal types are to be processed the circuitry shown in FIG. 2 can be used. In other words, three oversampling demodulator 36 are provided, and the timing signals 68 are used to activate separate oversampling demodulators 36 for each signal type, i.e., visible red, infrared or noise. Any number of oversampling demodulators 36 can be used depending on the selected number of signal types. Further, an oversampling demodulator 36 can be used to process multiple signal types through controlled use of timing signal 68 as deemed necessary.

The above discussion and related illustrations are directed primarily to preferred embodiments and practices of the invention. However, it is believed that numerous changes and modifications in the actual implementation of the concepts described will be apparent to those skilled in the art, and it is contemplated that such changes and modifications may be made without departing from the scope of the invention as defined by the following claims.

What is claimed is:

1. An oximeter including a light emitting means and a photosensor means for converting received pulses of light from said light emitting means to an electrical signal having a dynamic range directly related to amplitudes of received pulses of light, said oximeter further comprising:
   an analog-to-digital converter means for providing digitized signals accurately representative of amplitudes of received pulses of light; and,
   filter means; and
   an oversampling demodulator means for providing a switched and filtered electrical signal from said photosensor means to said analog-to-digital converter means, said oversampling demodulator means including switching means for alternately connecting said electrical signal from said photosensor means to ground and to said filter means, said filter means having a cutoff frequency below both cycle rates for said electrical signal from photosensor means and switching rates of said switching means.

2. An oximeter according to claim 1 further including a pulse control module means for providing timing signals to control pulsing of light from said light emitting means and for also synchronizing said switching means for switching of said electrical signal with pulsing of light from said light emitting means.

3. An oximeter according to claim 2 further including a readout means; and
   a central processor unit means which sends initial timing signals to said pulse control module means and display signals, responsive to said digitized signals from said analog-to-digital converter means, to said readout means, said central processor unit means sends no other signals for control of circuits used in said oximeter.

4. An oximeter including a light emitting means and a photosensor means for converting received pulses of light from said light emitting means to an electrical signal having a dynamic range directly related to amplitudes of received pulses of light, said oximeter further comprising:
   an analog-to-digital converter means for providing digitized signals accurately representative of amplitudes of received pulses of light;
   filter means;
   an oversampling demodulator means for providing a switched and filtered electrical signal from said photosensor means to said analog-to-digital converter means;
   a queued serial input module means for receiving digitized signals from said analog-to-digital converter means;
   a central processor unit means; and
   a random access memory means;
   said queued serial input module means having an interface with said central processor unit means through said random access memory means.

5. A pulse oximeter including a central processor unit means for calculating oxygen saturation in blood, said pulse oximeter further comprising:
   a light emitting means and a photosensor means for converting received pulses of light from said light emitting means to an electrical signal having a dynamic range directly related to amplitudes of received pulses of light;

an analog-to-digital converter means for providing digitized signals accurately representative of amplitudes of received pulses of light;

filter means; and an oversampling demodulator means for providing a switched and filtered electrical signal from said photosensor means to said analog-digital converter means; said oversampling demodulator means includes switching means for alternately connecting said electrical signal from said photosensor means to ground and to said filter means, said filter means having a cutoff frequency below both cycle rates for said electrical signal from said photosensor means and switching rates of said switching means.

6. Pulse oximeter according to claim 5 further including a pulse control module means for providing timing signals to control pulsing of light from said light emitting means and for also synchronizing said switching means for switching of said electrical signal with pulsing of light from said light emitting means.

7. A pulse oximeter including a central processor unit means for calculating oxygen saturation in blood, said pulse oximeter further comprising:

a light emitting means and a photosensor means for converting received pulses of light from said light emitting means to an electrical signal having a dynamic range directly related to amplitudes of received pulses of light;

an analog-to-digital converter means for providing digitized signals accurately representative of amplitudes of received pulses of light;

filter means; and an oversampling demodulator means for providing a switched and filtered electrical signal from said photosensor means to said analog-digital converter means;

a queued serial input module means for receiving digitized signals from said analog-to-digital converter means; and a random access memory means providing an interface for said queued serial input module means with said central processor unit means.

8. A method for measuring electrical pulse signal amplitudes produced from energy sensor means that have received energy from energy emitter means for digital processing using at least one analog-to-digital converter means without having to compare a first dynamic range for said electrical pulse signal amplitudes with a second dynamic range for said analog-to-digital converter means and then adjust gain of at least one amplifier to have said first dynamic range be within said second dynamic range, including the steps of:

amplifying said electrical pulse signal amplitudes using an input amplifier means;

switching said amplified electrical pulse signal amplitudes between ground and a filter means;

filtering said switched electrical pulse signal amplitudes through said filter means having a cutoff frequency below both cycle rates for said electrical pulse signal from said energy sensor means and switching rates used to switch said electrical pulse signal amplitudes;

providing a timing signal from a pulse control module means to control pulsing of energy from said energy emitter means and for also synchronizing said switching of said electrical signal with pulsing of said light; and, digitizing signals output from said filter means using said analog-digital converter means.

9. The method as defined in claim 8 further including the step of:

inputting said digitized signals output from said analog-to-digital converter means to a queued serial input module means having an interface with a central processor unit means through a random access memory means.

10. A pulse energy measuring system including an energy emitting means and an energy sensor means for converting received energy from said energy emitting means to an electrical signal, said pulse energy measuring system further comprising:

filter means;

switching means for alternately connecting said electrical signal from said energy sensor means to ground and to said filter means, said filter means having a cutoff frequency below both cycle rates for said electrical signal from said energy sensor means and switching rates of said switching means;

timing means for producing a timing signal that controls pulsing of energy received by said energy sensor means and that also synchronizes switching of said switching means with pulsing of energy received by said energy sensor means; and analog/digital converter means for converting analog signals from said filter means to digital signals.

11. A pulse energy measuring system according to claim 10 further comprising at least two of said energy emitting means.

12. A pulse energy measuring system according to claim 10 wherein said switching rates of said switching means are at least two times faster than said cycle rates of electrical signals from said energy sensor means.

13. A pulse energy measuring system according to claim 10 further comprising a microcontroller/processor means including said timing means, a queued input means for receiving digitized output from said analog/digital converter means, a random access memory means and a central processor means wherein said central processor means is interconnected with said timing means and said queued input means through said random access memory means.

14. An oximeter including a light emitting means and a photosensor means for converting received light from said light emitting means to an electrical signal, said oximeter further comprising:

switching means for alternately connecting said electrical signal from said photosensor means to ground and to said filter means, said filter means having a cutoff frequency below both cycle rates for said electrical signal from said photosensor means and switching rates of said switching means;

timing means for producing a timing signal that controls pulsing of light received by said photosensor means and that also synchronizes switching of said switching means with pulsing of light received by said photosensor means; and, analog/digital converter means for converting analog signals from said filter means to digital signals.

15. A oximeter according to claim 14 further comprising at least two of said light emitting means.

16. An oximeter according to claim 14 further comprising at least two of said filter means and at least two of said switching means that are synchronized with pulsing of said light received by said photosensor means using timing signals from said timing means, and each of said switching means being connected to one of said filter means having cutoff frequencies below both cycle rates for said electrical signal from said photosensor means and switching rates of said connected switching means.

17. An oximeter according to claim 14 wherein said switching rates of said switching means are at least ten times faster than said cycle rates of electrical signals from said photosensor means.

18. An oximeter according to claim 14 wherein said cutoff frequency of said filter means is less than 20 Hz.

19. An oximeter according to claim 14 further comprising a microcontroller/processor means including said timing means, a queued input means for receiving digitized output from said analog/digital converter means, a random access memory means and a control processor means wherein said central processor means is interconnected with said timing means and said queued input means through said random access memory means.

20. A method for measuring electrical pulse signal amplitudes produced from energy sensor means that have received energy from an energy emitter means, said method including the steps of:
  switching said electrical pulse signal between ground and filter means;
  filtering said switched electrical pulse signal through said filter means having a cutoff frequency below both cycle rates for said electrical pulse signal from said energy sensor means and switching rates used to switch said electrical pulse signal;
  providing a timing signal to control pulsing of energy from said energy emitter means and to also synchronize said switching of said electrical pulse signal with pulsing of said energy; and,
  digitizing signals output from said filter means.

21. The method as defined in claim 20 wherein said switching rates are at least ten times faster than said cycle rates.

22. A method for pulsed in vivo measurement of blood oxygenation saturation levels using at least one light source means and a photosensor means, including the steps of:
  switching electrical signals from said photosensor means between ground and a filter means;
  filtering said switched electrical signal through said filter means having a cutoff frequency below both cycle rates for said electrical signal from said photosensor means and switching rates used to switch said electrical signal;
  providing a timing signal to control pulsing of light from said light source means and for also synchronizing said switching of said electrical signal with pulsing of said light; and,
  digitizing signals output from said filter means.

23. The method as defined in claim 22 wherein said switching rates are at least two times faster than said cycle rates.

* * * * *